United States Patent [19]

Das et al.

[11] Patent Number: 4,524,151
[45] Date of Patent: Jun. 18, 1985

[54] 7-OXABICYCLOHEPTANE THIO ETHERS USEFUL AS CARDIOVASCULAR AGENTS

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 551,636

[22] Filed: Nov. 14, 1983

[51] Int. Cl.³ .................. C07D 307/00; A61K 31/34
[52] U.S. Cl. ..................................... 514/469; 549/463
[58] Field of Search ........................ 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off.
2039909 8/1980 United Kingdom.

Primary Examiner—Henry R. Jiles
Assistant Examiner—Barnard I. Dentz
Attorney, Agent, or Firm—Lawrence S. Levinson; Burton Rodney

[57] ABSTRACT

7-Oxabicycloheptane ethers of prostaglandin analogs are provided having the structural formula

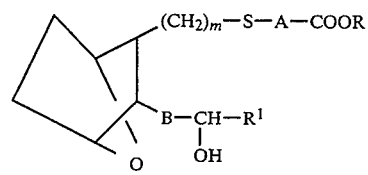

and including all stereoisomers thereof.

The compounds are cardiovascular agents useful, for example, in the treatment of thrombolytic disease.

16 Claims, No Drawings

7-OXABICYCLOHEPTANE THIO ETHERS USEFUL AS CARDIOVASCULAR AGENTS

DESCRIPTION OF THE INVENTION

The present invention relates to 7-oxabicycloheptane thio ethers which are cardiovascular agents useful, for example, in the treatment of thrombolytic disease. These compounds have the structural formula

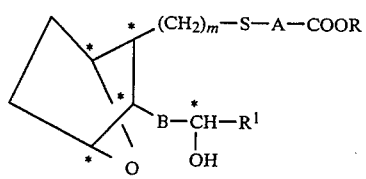

and including all stereoisomers thereof, wherein m is 1 to 4; A is $(CH_2)_n$ or $-(CH_2)_n$, $-CH=CH-$; n is 1 to 8; n' is 1 or 2; R is H, lower alkyl or alkali metal; B is $-(CH_2)_2-$ or $-CH=CH-$; and $R^1$ is lower alkyl, aryl, arylalkyl, cycloalkyl or cycloalkylalkyl.

Thus, some of the compounds within the scope of the present invention may have the following structures:

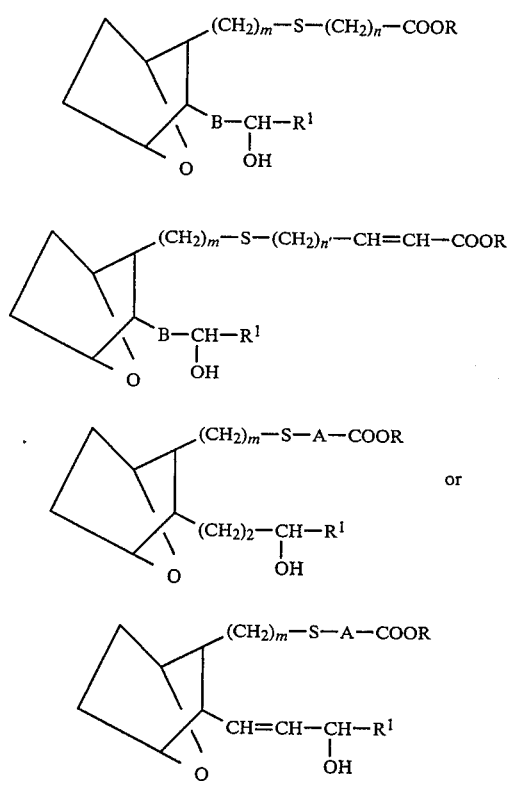

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens. 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "cycloalkylalkyl" as used herein refers to cycloalkyl groups as defined above linked to an alkyl group as defined above.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" include straight or branched chain radicals having from 1 to 4 carbons in the normal chain in the case of "$(CH_2)_m$" and 1 to 8 carbons in the normal chain in the case of "$(CH_2)_n$", and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

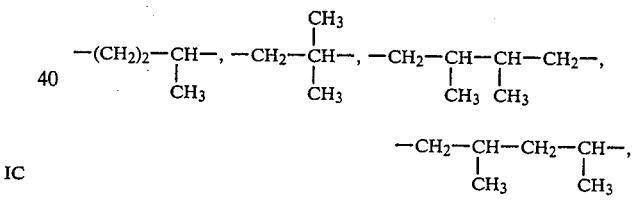

and the like.

Preferred are those compounds of formula I wherein A is $-CH=CH-$ or $-(CH_2)_2-$, m is 1 or 2, B is $-CH=CH-$ or $-(CH_2)_2$, R is hydrogen and $R^1$ is lower alkyl, ph enyl or benzyl.

The various compounds of the invention may be prepared as outlined below.

The 7-oxabicycloheptane thio ether compounds of formula I of the invention wherein $(CH_2)_m$ is $(CH_2)_2$ and A is $CH_2-CH=CH-$ or $(CH_2)_n$ and B is $CH=CH$ may be prepared starting with the cyanoalcohol II

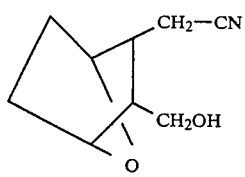

which is subjected to a silylation wherein compound II is reacted with a t-butyldimethylsilyl chloride having the structure A

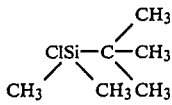

A in the presence of dry dichloromethane and triethylamine and 4-dimethylaminopyridine to form the silyl ether

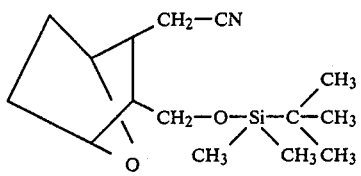

III which is reduced by treating with a reducing agent such as diisobutylaluminum hydride, in the presence of an inert organic solvent such as toluene, tetrahydrofuran or methylene chloride in an inert atmosphere, at reduced temperatures of from about −78° C. to about 0° C. to form the aldehyde IV

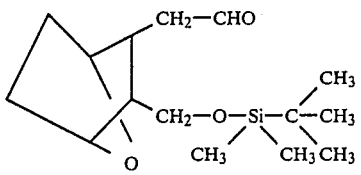

IV

The aldehyde IV is further reduced by treatment with a reducing agent such as lithiumaluminum hydride, sodium borohydride or lithium borohydride in the presence of an inert organic solvent such as tetrahydrofuran, ethanol or ether to form the alcohol V

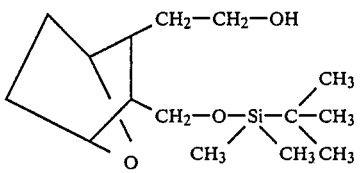

V

The alcohol V is then subjected to a modified Mitsonubu reaction wherein a mixture of the alcohol V and thioloacetic acid in an inert solvent such as tetrahydrofuran, ether or toluene is reacted with a mixture of triphenylphosphine and diisopropylazo dicarboxylate in an inert organic solvent such as tetrahydrofuran, ether or toluene at reduced temperatures of from about 0° C. to about 25° C. to form thioacetate VI

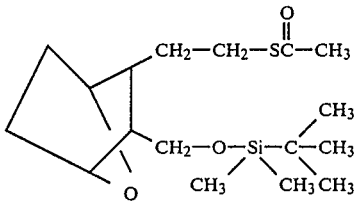

VI

The silyl group is removed from thioacetate VI by reacting VI with tetra-n-butylammonium fluoride trihydrate in the presence of an inert organic solvent such as tetrahydrofuran or ether to form alcohol thioacetate VII

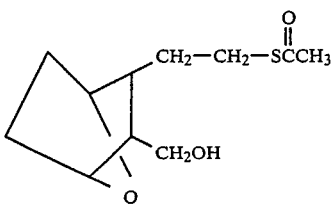

VII which is then deacetylated by treating with lithium aluminum hydride, potassium carbonate or sodium methoxide in the presence of an inert organic solvent such as tetrahydrofuran or methanol to form thiol VIII

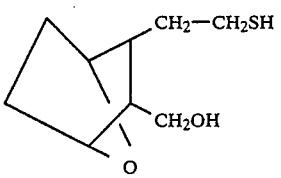

VIII

The thiol VIII is then alkylated by reacting same with an alkylating agent of the structure IX

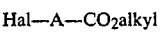

Hal—A—CO$_2$alkyl     IX in the presence of a base such as sodium or potassium carbonate in the case where A is —CH=CH—, or sodium or potassium hydride in the case where A is (CH$_2$)$_n$, and an inert organic solvent such as acetone, THF or DMF, and reduced temperatures of from about 0° C. to about 50° C., to form alcohol X

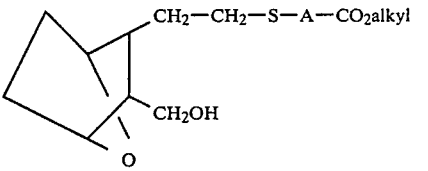

X which is subjected to a Corey-Kim oxidation wherein alcohol X in toluene is added to a mixture of dimethylsulfide and N-chlorosuccinimide in dry toluene or other inert organic solvent such as methylene chloride, and the mixture is stirred at 0° C. and then cooled to −25° C. After stirring at −25° C., triethylamine is added and the mixture is then warmed and concentrated to give aldehyde XI

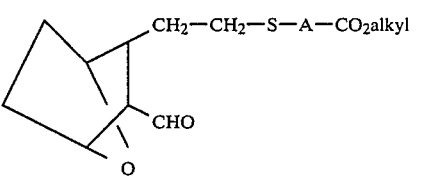

XI

Aldehyde XI is then made to undergo a phosphonate reaction as follows. A slurry of base such as sodium hydride, potassium hydride, sodium methoxide or potassium t-butoxide in mineral oil, and dry dimethoxyethane containing a phosphonate of the structure XII

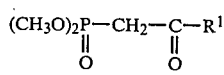   XII is reacted with a solution of aldehyde XI in an inert organic solvent such as dimethoxy ethane to form enone XIII

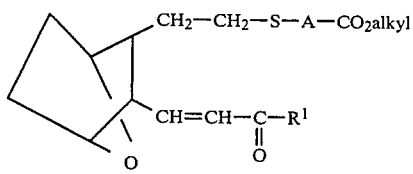   XIII which is reduced by reaction with cerium trichloride and sodium borohydride in the presence of an alkanol solvent such as methanol or ethanol to form ester XIV

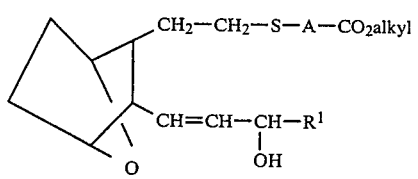   XIV

Ester XIV may then be hydrolyzed by reaction with an alkali metal hydroxide such as NaOH, KOH or LiOH to form the corresponding alkali metal salt which may then be neutralized with an acid such as HCl or oxalic acid to form the corresponding acid XV

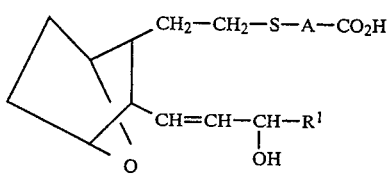   XV

Alternatively, compounds of the invention wherein A is (CH₂)₃ may be prepared by reacting thiol VIII with an alkylating agent of the structure IXA

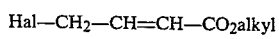   IXA in the presence of a weak base such as Na₂CO₃ as described above to form alcohol XA

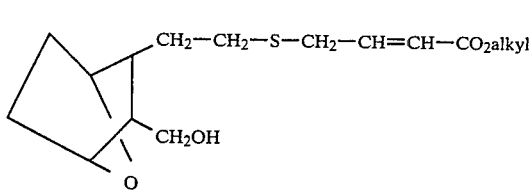   XA which is hydrogenated by reaction with hydrogen in the presence of a catalyst such as palladium on charcoal in methanol to form the saturated ester XVI

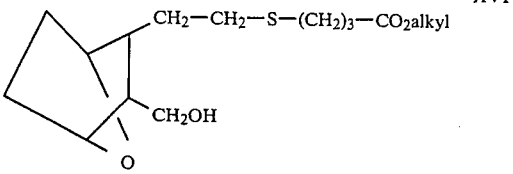   XVI

Then following the reaction sequence (as described above with respect to ester X), the saturated ester XVI is subjected to a Corey-Kim oxidation as described above to form aldehyde XVII

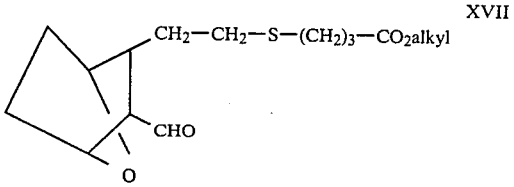   XVII which is made to undergo a phosphonate reaction (as described above with respect to aldehyde XI) to form enone XVIII

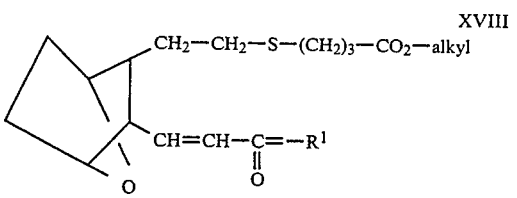   XVIII which is then reduced (as described above with respect to compound XIII) to form ester XIX

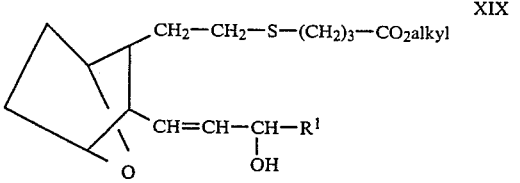   XIX which may then be hydrolyzed (as described above with respect to compound XIV) to form the corresponding alkali metal salt, and finally the corresponding acid XX

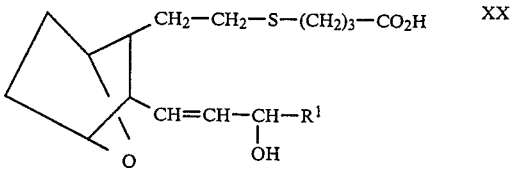   XX

Compounds of formula I wherein m is other than 1, that is, m is 3 or 4, may be prepared by subjecting aldehyde IV to a homologation sequence, such as a Wittig reaction with (C₆H₅)₃P=CHOMe followed by hydrolysis (m-1) times. The aldehyde IVA

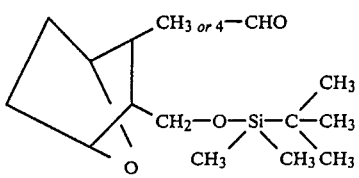                                IVA may then be carried on to compounds of this invention wherein m is 3 or 4 by subjecting IVA to the reduction step, followed by the modified Mitsonubu reaction and so forth as described above with respect to conversion of aldehyde IV to the compounds of the invention.

Compounds of the invention wherein $(CH_2)_m$ is $CH_2$ and B is $CH=CH$ may be prepared by subjecting alcohol XXI

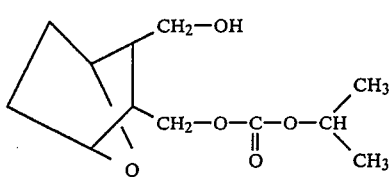                                XXI to a modified Mitsonubu reaction is described above with respect to alcohol V to form thioacetate XXII

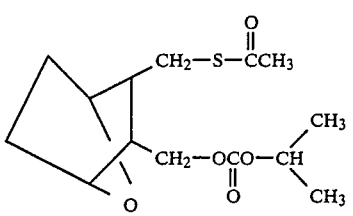                                XXII which is then reduced by treating with lithium aluminum hydride or diborane in the presence of an inert organic solvent such as tetrahydrofuran or other solvent such as ether to form the thiol XXIII

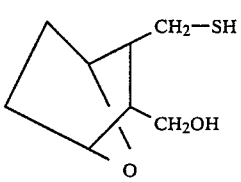                                XXIII

Thiol XXIII is then alkylated by reacting with alkylating agent IX

Hal—A—CO$_2$alkyl                           IX as described above with respect to thiol VIII to form alcohol XXIV

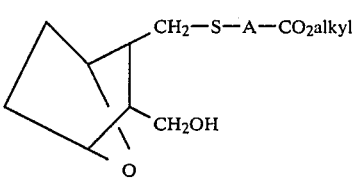                                XXIV

Alcohol XXIV is subjected to a Swern oxidation wherein it is reacted with a mixture of oxalyl chloride in methylene chloride and dimethylsulfoxide at reduced temperatures of from about −50° to about −78° C. Triethylamine is added and the mixture is warmed to form aldehyde XXV

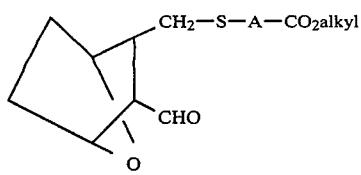                                XXV

The aldehyde XV is then subjected to a phosphonate reaction as described with respect to aldehyde XI to form enone XXVI

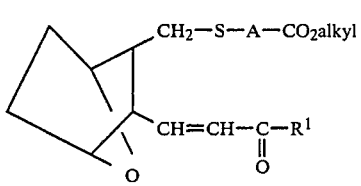                                XXVI which is reduced in the presence of cerium trichloride, sodium borohydride and methanol as described with respect to enone XIII to form ester XXVII

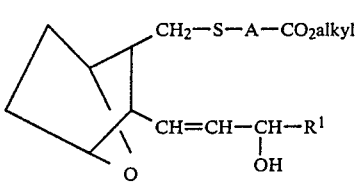                                XXVII

Ester XXVII may be hydrolyzed to the corresponding alkali metal salt and acid XXVIII as described with respect to ester XIV

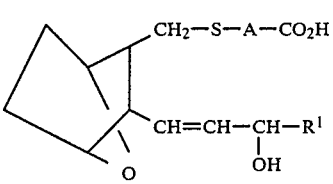                                XXVIII

To prepare compounds of formula I wherein A is $(CH_2)_n$ and B is $—(CH_2)_2—$, that is

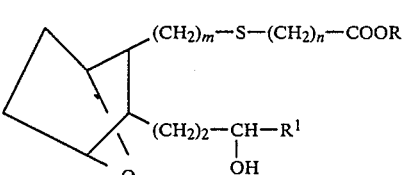                               I' compounds of the structure

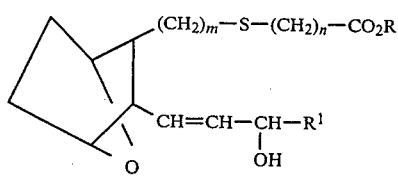

I"

may be catalytically reduced by reacting same with hydrogen in the presence of a palladium on carbon catalyst to form XXIX

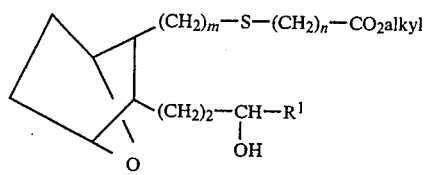

XXIX

Compound XXIX is then treated with an alkali metal hydroxide such as lithium hydroxide, sodium hydroxide or potassium hydroxide to form the corresponding alkali metal salt followed by neutralization with an acid such as dilute HCl or oxalic acid to form the corresponding acid.

The starting cyano carbonate B, that is

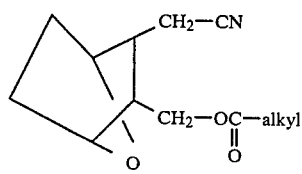

B used in preparing compounds of the invention wherein $(CH_2)_m$ is $(CH_2)_2$, A is $-CH_2-CH=CH-$ or $(CH_2)_n$ and B is $CH=CH$ may be prepared as follows.

The mesoanhydride

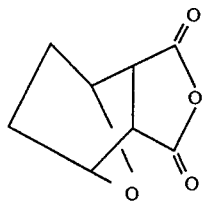

C is reduced by reacting same with a reducing agent such as lithium aluminum hydride, lithium borohydride, diisobutylaluminum hydride or diborane in the presence of an inert solvent such as tetrahydrofuran, ether or toluene to form the diol D (which may be used as the starting material for compounds wherein m is 1)

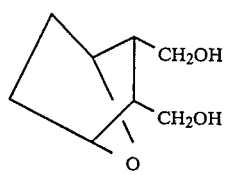

D which is subjected to a chloroformylation reaction by reacting the diol with phosgene in the presence of an inert solvent such as tetrahydrofuran, toluene, benzene or methylene chloride or a mixture thereof to form chloroformate E

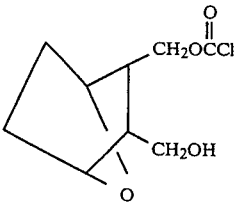

E

Chloroformate E is made to undergo cyclic-carbonate formation by reacting E with pyridine in the presence of dichloromethane to form the cyclic-carbonate F

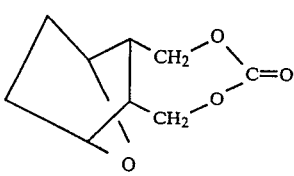

F which undergoes alcoholysis by reaction with an alkanol such as isopropanol to form alcohol XXI (which is employed as the starting material for forming compounds of the invention wherein m is 1, A is $(CH_2)_n$ and B is $CH=CH$)

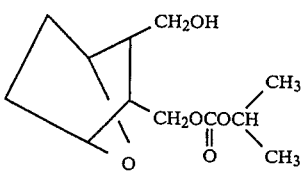

XXI

Upon reacting XXI with tosyl chloride in the presence of a base such as pyridine, dimethylaminopyridine or 2,6-lutidine, the tosylate XXX is formed

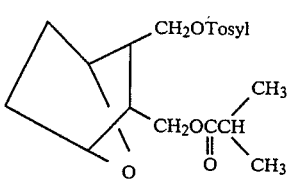

XXX

The tosylate XXX is then reacted with sodium cyanide or potassium cyanide in the presence of an inert solvent such as dimethyl sulfoxide to form the cyanide XXXI

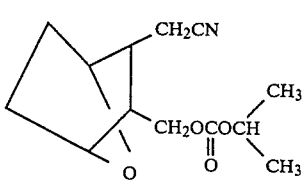

XXXI which may then be hydrolyzed by reaction with a basic salt such as potassium carbonate or sodium carbonate in the presence of methanol to form the starting material II.

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

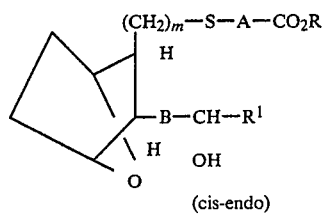

(cis-endo) Ia

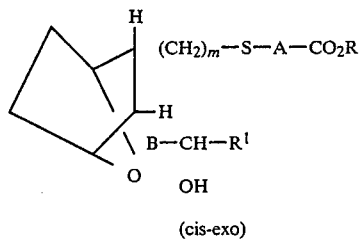

(cis-exo) Ib

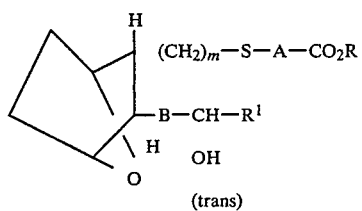

(trans) Ic

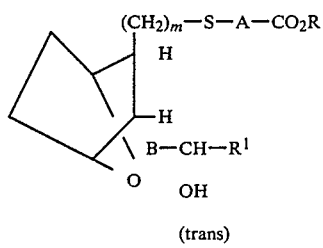

(trans) Id

The wavy ( ) line in the above formulae indicates that the hydroxy group in each of the compounds of formulae Ia-Id is either R($\beta$) or S($\alpha$).

The nucleus in each of the compounds of the invention is depicted as

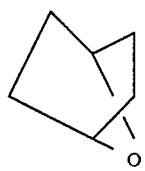

for matter of convenience; it will also be appreciated that the nucleus in the compounds of the invention may be depicted as

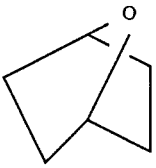

The compounds of this invention are cardiovascular agents useful as platelet aggregation inhibitors, such as arachidonic acid-induced platelet aggregation, e.g., for treatment of thrombolytic disease, such as coronary or cerebral thromboses. In addition, the compounds of the invention are useful in inhibiting bronchoconstruction such as associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following working Examples represent preferred embodiments of the invention. All temperatures are expressed in degrees Centigrade unless otherwise indicated.

EXAMPLE 1

[1α,2β,3β(1E,3R),4α]-4-[[[3-(3-Hydroxy-4,4-dimethyl-1-octenyl)-7-oxabicyclo[2.2.1]hept-2-yl]ethyl]thio]-2-butenoic acid, methyl ester

A.

(1α,2β,3β,4α)-cis-exo-3-Isopropyloxycarbonyloxymethyl-2-hydroxymethyl-7-oxabicyclo[2.2.1]heptane To a suspension of 11.4 g of lithium aluminum hydride (300 mmole, 1.6 eq) in 400 ml of dry THF at 0° C. was added dropwise a solution of 32 g (1α,2β,3β,4α)-cis-exo-[7-oxabicyclo[2.2.1]hept-2-yl]-2,3-dicarboxylic acid anhydride (mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of (1α,2β,3β,4α)-cis-exo-7-oxabicyclo[2.2.1]heptane-2,3-dimethanol (meso-diol) as a colorless solid.

To a solution of 10 g (63.2 mmole) of meso-diol in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give a crude oil of (1α,2β,3β,4α)-cis-exo-3-chlorocarbonyloxy-2-hydroxymethyl-7-oxabicyclo[2.2.1]heptane.

This oil was dissolved in 30 ml of dry $CH_2Cl_2$ and cooled to −50° C. To this solution was added dropwise a solution of 10 ml pyridine in 10 ml $CH_2Cl_2$. It was stirred for 10 minutes and quenched with $H_2O$. The mixture was extracted thoroughly with $CH_2Cl_2$. The organic extract was dried over $MgSO_4$ and concentrated to give (1α,2β,3β,4α)-7-oxabicyclo[2.2.1]heptane 2,3-dimethane carbonate (cyclic carbonate) as a crystalline solid (10.7 g).

A mixture of 10.7 g of (1α,2β,3β,4α)-cis-exo-7-oxabicyclo[2.2.1]heptane 2,3-dimethane carbonate (cyclic carbonate) (58.1 mmole) in 100 ml isopropanol was refluxed for 24 hours. Excess isopropanol was removed under reduced pressure to give 14.4 g title A compound (hydroxycarbonate) as a viscous oil.

B.

(1α,2β,3β,4α)-cis-exo-3-Isopropyloxycarbonyloxymethyl-2-p-toluenesulfonyloxymethyl-7-oxabicyclo[2.2.1]heptane To a solution of 19.7 g of title A alcohol (80 mmole) in 30 ml $CH_2Cl_2$ and 12.8 ml pyridine (160 mmole, 2 eq.) was added 18.5 g p-toluenesulfonyl chloride (96 mmole, 1.2 eq.). The mixture was stirred at 25° C. for 36 hours then diluted with 200 ml ether, and washed with 100 ml brine.

The organic layer was dried over $MgSO_4$ and concentrated to give 32.8 g of title crude tosylate as an oil.

C.

(1α,2β,3β,4α)-cis-exo-3-Isopropyloxycarbonyloxymethyl-2-cyanomethyl-7-oxabicyclo[2.2.1]heptane To a solution of 24.0 title B crude tosylate (60 mmole) in 20 ml DMSO was added with stirring 6.0 g powdered sodium cyanide (120 mmole, 2 eq.). The mixture was heated at 90°–95° C. for 1.5 hours under an argon atmosphre. The cooled mixture was diluted with 50 ml water and extracted with five 100 ml portions of ether. The ethereal extracts were dried over anhydrous $MgSO_4$ and filtered though a bed of florosil. The filtrate was concentrated, and the residue was recrystallized with ether/hexanes to give 8.4 g of title cyanocarbonate as a light yellow crystalline solid.

D.

(1α,2β,3β,4α)-cis-exo-3-Hydroxymethyl-2-cyanomethyl-7-oxabicyclo[2.2.1]heptane

To 8.4 g of title C cyanocarbonate (33.2 mmole) was added 75 ml of a 1% solution of potassium carbonate in methanol-water (2:1). The reaction mixture was stirred at 25° C. for 6 hours, then acidified with 2N HCl solution, saturated with sodium chloride and extracted with six 100 ml portions of $CH_2Cl_2$. The combined organic layer was dried over anhydrous $MgSO_4$ and concentrated to give 5.5 g of crude title cyanoalcohol as a light yellow oil.

E.

(1α,2β,3β,4α)-cis-exo-3-t-Butyldimethylsilyloxymethyl-2-cyanomethyl-7-oxabicyclo[2.2.1]heptane To a solution of 5.0 g title D alcohol (30 mmole) in 50 ml of dry $CH_2Cl_2$ and 10 ml of triethylamine (70 mmole, 3.3 eq.) at 0° C. was added with stirring 490 mg 4-dimethylaminopyridine (4 mmole) and 5.28 g t-butyldimethylsilyl chloride (35 mmole, 1.16 eq.). The reaction mixture was slowly warmed to 25° C. and stirred for 18 hours, then diluted with 200 ml ether and filtered through a small bed of anhydrous $MgSO_4$. The filtrate was concentrated. Purification was done on a silica gel column, eluting with 15% ethyl acetate/hexanes to give 10.25 g of title silyl ether as a light yellow oil.

F.

(1α,2β,3β,4α)-cis-exo-3-t-Butyldimethylsilyloxymethyl-2-formyloxymethyl-7-oxabicyclo[2.2.1]heptane To a solution of 10.0 g of title E silyl ether (26.2 mmole) in 30 ml of dry toluene at −78° C. under an argon atmosphere was added dropwise 25 ml of a 25% by weight solution of diisobutylaluminum hydride (44 mmole, 1.6 eq.) in toluene. The mixture was stirred at −78° C. for 4 hours, quenched at −78° with a saturated solution of ammonium chloride, warmed to 0° C. and acidified with 1N HCl solution, extracted with three 100 ml portions of $CH_2Cl_2$, dried over anhydrous $MgSO_4$ and concentrated to give 9.3 g of crude title aldehyde.

G.

(1α,2β,3β,4α)-cis-exo-[3-t-Butyldimethylsilyloxymethyl-7-oxabicyclo[2.2.1]hept-2-yl]ethanol To 9.3 g crude title F aldehyde (32.7 mmole) in 30 ml of dry THF at 0° C. under an argon atmosphere was added portionwise 1.0 g lithium aluminum hydride (26.0 mmole, 3.2 eq.) with stirring. The reaction mixture was stirred while being warmed to 25° C. over a period of 1 hour, quenched by slow addition of a saturated sodium sulfate at 0° C., dried over anhydrous $MgSO_4$ and filtered. The solid was washed with $CH_2Cl_2$. The combined filtrate was concentrated to give a crude oil. This oil was purified on a silica gel column, eluting with 30% EtOAc/hexanes to give 8.55 g title alcohol as a colorless oil.

H.

(1α,2β,3β,4α)-[[3-t-Butyldimethylsilyloxymethyl-7-oxabicyclo[2.2.1]hept-2-yl]ethyl]methylthioacetate To a solution of 5.25 g triphenylphosphine (20 mmole, 2 eq.) in 60 ml dry THF at 0° C. was added dropwise 4.16 g diisopropylazo dicarboxylate (20 mmole, 2 eq.) over a period of 15 minutes. The mixture was stirred at 0° C. for 30 minutes then to it was added dropwise a solution of 2.6 g title G alcohol (10 mmole) and 1.45 ml of thiolacetic acid (20 mmole, 2 eq.) in 10 ml dry THF. The reaction mixture was stirred at 0° C. for 1 hour and 25° C. for 3 hours, then concentrated. The residue was triturated with ether/hexane, filtered, and the filtrate was concentrated and purified on a silica gel column, eluting with 10% EtOAc/hexanes to give 2.3 g title thioacetate as a light yellow oil.

I.
(1α,2β,3β,4α)-[[3-Hydroxymethyl-7-oxabicyclo[2.2.1-]hept-2-yl]ethyl]methylthioacetate To a solution of 2.3 g title H thioacetate (6.7 mmole) in 20 ml dry THF at 0° C. was added 2.23 g tetra-n-butylammoniumfluoride trihydrate (7.07 mmole, 1.05 eq.) in 5 ml dry THF. The reaction mixture was warmed at 25° C. and stirred for 18 hours, diluted with 100 ml ether and washed with 30 ml saturated NaHCO₃ solution, dried over anhydrous MgSO₄ and concentrated to give a crude oil.

Purification was done on a silica gel column, eluting with 20% EtOAc/hexanes then 50% EtOAc/hexanes to give 1.22 g title alcohol thioacetate as a colorless oil.

J.
(1α,2β,3β,4α)-[3-Hydroxymethyl-7-oxabicyclo[2.2.1-]hept-2-yl]ethanethiol To a slurry of 200 mg lithium aluminum hydride (5.27 mmole, 4 eq.) in 20 ml dry THF at 0° C. was added a solution of 1.22 g title I thioacetate (5.3 mmole) in 5 ml THF dropwise under an argon atmosphere. The reaction mixture was stirred at 0° C. for 1 hour, then quenched with a saturated sodium sulfate solution, dried with anhydrous MgSO₄, then filtered. The filtrate was concentrated to give 900 mg title thiol as a colorless oil.

K.
(1α,2β(5E),3β,4α)-4-[[[3-Hydroxymethyl-7-oxabicyclo[2.2.1]hept-2-yl]ethyl]thio]-2-butenoic acid, methyl ester To a slurry of 1.38 g of dried and powdered potassium carbonate (10 mmole, 2.1 eq.) in 20 ml dry acetone at 0° C. was added a solution of 900 mg title J thiol (4.8 mmole) in 5 ml acetone, followed by 1.75 ml of methyl-4-bromocrotonate (15 mmole, 3 eq.). The reaction mixture was stirred at 0° C. for 10 hours, then diluted with 100 ml ether and filtered through a pad of anhydrous MgSO₄. The filtrate was concentrated. The residue was purified on a silica gel column, eluting with 20% EtOAc/hexanes and 50% EtOAc/hexanes to give 823 mg of title alcohol as a colorless oil.

L.
[1α,2β(5E),3β,4α]-4-[[[3-Formyl-7-oxabicyclo[2.2.1-]hept-2-yl]ethyl]thio]-2-butenoic acid, methyl ester To a solution of 734.2 mg N-chlorosuccinimide (5.24 mmole, 5 eq.) in 30 ml dry toluene at 0° C. under an argon atmosphere was added 359.7 mg dimethylsulfide (5.76 mmole, 5.5 eq.). The mixture was stirred for 30 minutes at 0° C. then cooled to −25° C. and a solution of 300 mg title K alcohol (1.05 mmole) in 20 ml toluene was added. After stirring at −25° C. for 3 hours, 729 μl of triethylamine was added. The mixture was warmed to 25° C. and stirred for 1 hour, then diluted with 100 ml ether, washed with two 20 ml portions of 1% HCl solution, 20 ml water, dried over anhydrous MgSO₄ and concentrated to give 400 mg of crude title aldehyde as an oil.

M.
[1α,2β(5E),3β(1E),4α]-4-[[[3-Oxo-4,4-dimethyl-1-octenyl)-7-oxabicyclo[2.2.1]hept-2-yl]ethyl]thio]-2-butenoic acid, methyl ester To a slurry of 72.6 mg of 50% sodium hydride in mineral oil (1.5 mmole, 1.1 eq.) in 10 ml dry dimethoxyethane at 0° C. was added 521 mg of 2-oxo-3,3-dimethyl heptyl dimethylphosphonate (2.04 mmole, 1.5 eq.). The mixture was stirred for 1 hour at 25° C., cooled to 0° C. and to it was added a solution of 400 mg crude title L aldehyde (ca. 1.36 mmole) in 5 ml DME. The reaction mixture was stirred for 2 hours at 25° C., then quenched with glacial acetic acid, concentrated, the residue diluted with 50 ml ether and washed with two 10 ml portions of saturated NaHCO₃, 10 ml H₂O, dried over anhydrous MgSO₄ and concentrated to give an oil. The oil was purified on a silica gel column, eluting with 30% ether/hexanes to give 225 mg title enone as an oil.

N.
[1α,2β,3β(1E,3R),4α]-4-[[[3-(3-Hydroxy-4,4-dimethyl-1-octenyl)-7-oxabicyclo[2.2.1]hept-2-yl]ethyl]thio]-2-butenoic acid, methyl ester and

O.
[1α,2β,3β(1E,3S),4α]-4-[[[3-(3-Hydroxy-4,4-dimethyl-1-octenyl)-7-oxabicyclo[2.2.1]hept-2-yl]ethyl]thio]-2-butenoic acid, methyl ester To 225 mg title M enone (0.55 mmole) in 2 ml dry methanol at 25° C. was added 202.6 mg cerium trichloride (0.55 mmole, 1 eq.). The mixture was stirred at 25° C. for 10 minutes then cooled to 0° C. 20.7 mg sodium borohydride (0.55 mmole, 4 eq.) was then added, and the reaction mixture was stirred for 15 minutes, poured into 100 ml of a saturated ammonium chloride solution and extracted with three 30 ml portions of ether. The combined ethereal extract was dried over anhydrous MgSO₄ and concentrated.

Purification and separation was done on a LPS-1 silica gel column eluting with 30% ether/hexanes to give 55 mg title N compound and 10 mg title O compound.

EXAMPLE 2
[1α,2β,3β(1E,3R),4α]-4-[[[3-(3-Hydroxy-4,4-dimethyl-1-octenyl)-7-oxabicyclo[2.2.1]hept-2-yl]ethyl]thio]-2-butenoic acid To a solution of 55 mg Example 1, title N, ester (0.13 mmole) in 4 ml THF and 1 ml H₂O, saturated with argon, at 0° C. was added dropwise 1.3 ml of 1N lithium hydroxide solution. The mixture was stirred at 25° C. for 3 hours. THF was evaporated and the residue was diluted with 5 ml H₂O, acidified to pH 3 with saturated oxalic acid, and extracted with three 20 ml portions of ether. The ethereal extract was washed with 10 ml H₂O, dried over anhydrous MgSO₄ and filtered through a pad of LPS-1 silica gel. The filtrate was concentrated to give 51 mg of title acid as an E and Z mixture of the α,β-unsaturated acid.

Anal. Calcd (includes 0.5 mole H₂O): C, 65.15; H, 9.20; S, 7.90. Found: C, 65.13; H, 8.49; S, 7.78.

EXAMPLE 3
[1α,2β,3β(1E,3R),4α]-4-[[[3-(3-Hydroxy-4,4-dimethyl-1-octenyl)-7-oxabicyclo[2.2.1]hept-2-yl]ethyl]thio]-butanoic acid, methyl ester

A.
(1α,2β,3β,4α)-4-[[[3-(3-Hydroxymethyl-7-oxabicyclo[2.2.1]hept-2-yl]ethyl]thio]butanoic acid, methyl ester A mixture of 570 mg of Example 1 Title K olefin (2.0 mmole) and 600 mg of 10% palladium over carbon in 10 ml methanol was shaken in a Parr bottle under 40 psi hydrogen pressure, at 25° C. for 18 hours and then filtered. The filtrate was concentrated to give 470 mg of the title saturated alcohol ester as an oil.

B.
(1α,2β,3β,4α)-4-[[[3-Formyl-7-oxabicyclo[2.2.1]hept-2-yl]ethyl]thio]butanoic acid, methyl ester To a solution of 1.14 g of N-chlorosuccinimide (8.14 mmole, 5 eq.) in 60 ml of dry toluene at 0° C., under an argon atmosphere, was added 559 mg dimethyl sulfide (8.95 mmole, 5.5 eq.). The mixture was stirred for 30 minutes at 0° C., then cooled to −25° C. A solution of 470 mg of title A ester alcohol (1.63 mmole) in 40 ml toluene was added. After stirring at −25° C. for 3 hours, 1.13 ml of triethylamine (8.14 mmole, 5 eq.) was added. The mixture was stirred for 1 hour, then diluted with 200 ml of ether and washed with two 40 ml portions of 1% HCl solution, 40 ml of water, dried over anhydrous MgSO₄ and concentrated to give 440 mg of title aldehyde as a yellow oil. This crude oil was used in the next step without purification.

C.
[1α,2β,3β(1E),4α]-4-[[[3-(3-Oxo-4,4-dimethyl-1-octenyl)-7-oxabicyclo[2.2.1]hept-2-yl]ethyl]thio]butanoic acid, methyl ester To a slurry of 85.2 mg of 50% sodium hydride in mineral oil (1.76 mmole, 1.1 eq.) in 10 ml of dry dimethoxyethane at 0° C. under an argon atmosphere was added 625.1 mg of 2-oxo-3,3-dimethylheptyl dimethyl phosphonate (2.45 mmole, 1.5 eq.). The mixture was stirred for 1 hour at 25° C., cooled to 0° C. and a solution of 440 mg of crude title B aldehyde (ca. 1.6 mmole) in 5 ml DME added. The reaction mixture was stirred for 2 hours at 25° C., then quenched with glacial acetic acid, and concentrated. The residue was diluted with 50 ml of ether and washed with two 10 ml portions of saturated NaHCO₃, 10 ml H₂O, dried over anhydrous MgSO₄ and concentrated to give an oil. Flash chromatographed on a silica gel column, eluting with 33% ether in hexane to give 127 mg of title enone as an oil.

D.
[1α,2β,3β(1E,3R),4α]-4-[[[3-(3-Hydroxy-4,4-dimethyl-1-octenyl)-7-oxabicyclo[2.2.1]hept-2-yl]ethyl]thio]butanoic acid, methyl ester To 120 mg of title C enone (0.29 mmole) in 2 ml of dry methanol at 25° C. was added 107 mg of cerium trichloride (0.29 mmole, 1 eq.). The mixture was stirred at 25° C. for 10 minutes and then cooled to 0° C. 11 mg of sodium borohydride (0.29 mmole, 4 eq.) was then added and the reaction mixture was stirred for 15 minutes, poured into 50 ml of a saturated ammonium chloride solution and extracted with three 20 ml portions of ether. The combined ethereal extract was dried over anhydrous MgSO₄ and concentrated.

Purification and separation was done on a LPS-1 silica gel column, eluting with 40% ether in hexane to give 35 mg of title allylic alcohol as a clear oil.

EXAMPLE 4

[1α,2β,3β(1E,3R),4α]-4-[[[3-(3-Hydroxy-4,4-dimethyl-1-octenyl)-7-oxabicyclo[2.2.1]hept-2-yl]ethyl]thio]butanoic acid To a solution of 35 mg Example 3 ester (84.9 μmole) in 4 ml THF and 1 ml H₂O, saturated with argon, at 0° C. was added dropwise 850 μl of a 1M lithium hydroxide solution. The mixture was stirred at 25° C. for 3 hours then concentrated. The residue was diluted with 5 ml H₂O, then acidified to pH 3 with a saturated oxalic acid solution and extracted with three 20 ml portions of ether. The ethereal extract was washed with 10 ml H₂O, dried over anhydrous MgSO₄ and filtered through a pad of LPS-1 silica gel. The filtrate was concentrated to give 24 mg of the title acid as an oil.

Anal Calcd (includes 0.52 moles H₂O): C, 64.78; H, 9.65; S, 7.86. Found: C, 64.78; H, 9.37; S, 7.46.

TLC: Silica gel; 5% MeOH/CH₂Cl₂: Rf~0.37.

EXAMPLE 5

[1α,2β,3β(1E,3R),4α]-5-[[[3-(3-Hydroxy-4,4-dimethyl-1-octenyl)-7-oxabicyclo[2.2.1]hept-2-yl]methyl]thio]pentanoic acid, methyl and ethyl esters

A.
(1α,2β,3β,4α)-cis-exo-[[3-Isopropyloxycarbonyloxymethyl-7-oxabicyclo[2.2.1]hept-2-yl]methyl]methylthioacetate To a solution of 10.5 g of triphenylphosphine (40 mmole, 2 eq.) in 100 ml of dry THF at 0° C. was added dropwise 8.5 g of 95% pure diisopropylazodicarboxylate (60 mmole, 2 eq.) over a period of 15 minutes. After stirring for 30 minutes, a solution of 4.88 g of Example 1 title A alcohol carbonate (20 mmole) and 1.43 g of distilled thiol acetic acid (40 mmole, 2 eq.) in 10 ml of dry THF was added dropwise over a period of 20 minutes. The mixture was stirred at 0° C. for 30 minutes and at 25° C. for 1 hour, and then concentrated. The residue was triturated with ether/hexane, and then filtered. The filtrate was concentrated and purified on a silica gel column, eluting with 5% ethyl acetate in hexane followed by 10% ethyl acetate in hexane to give 5.12 g of title thioacetate as a colorless crystalline solid.

B.
(1α,2β,3β,4α)-cis-exo-[3-Hydroxymethyl-7-oxabicyclo[2.2.1]hept-2-yl]methanethiol To a slurry of 400 mg of 95% pure lithium aluminum hydride (13 mmole, 4.2 eq.) in 25 ml of dry THF at 0° C. under an argon atmosphere was added dropwise a solution of 1.9 g of title A thioacetate (6 mmole) in 100 ml of dry THF. The mixture was stirred at 0° C. for 30 minutes and at 25° C. for 1 hour and then quenched with a saturated sodium sulfate solution. The mixture was dried with anhydrous MgSO₄ and filtered. The filtrate was concentrated to give the crude title thio-alcohol as an oil.

This oil was used in the next step without purification.

C.
(1α,2β,3β,4α)-5-[[[3-Hydroxymethyl-7-oxabicyclo[2.2.1]hept-2-yl]methyl]thio]pentanoic acid, methyl and ethyl esters To a slurry of 480 mg of 50% sodium hydride in mineral oil (10 mmole, 2.1 eq.) in 20 ml of dry THF at 0° C. was added dropwise a solution of 820 mg of title B thioalcohol (4.71 mmole) in 5 ml of dry THF. After stirring for 20 minutes at 0° C., a solution of 3.17 ml of ethyl-5-bromovalerate (20 mmole, 4.2 eq.) was added dropwise. The reaction mixture was stirred at 0° C. for 2 hours and then quenched with a saturated solution of ammonium chloride. The layers were separated. The aqueous layer was acidified with a 2N HCl solution and extracted several times with CH₂Cl₂. The combined organic layer was dried over anhydrous MgSO$_4$ and concentrated. The residue was diluted with 25 ml of ether and treated with an etheral solution of diazomethane.

Purification was done on a silica gel column, eluting with 10% EtOAc/hexane followed by 20% EtOAc/hexane to give 540 mg of a mixture of title methyl and ethyl ester as a colorless oil.

D.
(1α,2β,3β,4α)-5-[[[3-Formyl-7-oxabicyclo[2.2.1]hept-2-yl]methyl]thio]pentanoic acid, methyl and ethyl esters To a solution of 400 ml of oxalyl chloride (3.5 mmole, 4 eq.) in 1 ml of dry CH$_2$Cl$_2$ at −60° C. was added dropwise 650 ml of dry dimethylsulfoxide (9 mmole, 10 eq.) over a period of 10 minutes. After stirring for 10 minutes, a solution of title E ester alcohol (350 mg, 0.87 mmole) in 1 ml of dry CH$_2$Cl$_2$ was added dropwise over a period of 5 minutes. The reaction mixture was stirred at −60° C. for 15 minutes and then to it was added 1 ml of distilled triethylamine (ca. 7 mmole). The mixture was warmed to 25° C. and then water was added and stirred for 30 minutes at 25° C. The mixture was diluted with methylene chloride and washed with a saturated solutin of sodium bicarbonate. The organic layer was dried over anhydrous MgSO$_4$ and concentrated.

The residue was purified on a silica gel column, eluting with 10–20% EtOAc/hexane to give 210 mg of the title aldehyde (mixture of methyl and ethyl esters).

E.
[1α,2β,3β(1E),4α]-5-[[[3-(3-Oxo-4,4-dimethyl-1-octenyl)-7-oxabicyclo[2.2.1]hept-2-yl]methyl]thio]pentanoic acid, methyl and ethyl esters To a slurry of 39.8 mg of 50% sodium hydride in mineral oil (0.8 mmole, 1.1 eq.) in 7 ml of dry dimethoxyethane at 0° C. under an argon atmosphere was added 283 mg of 2-oxo-3,3-dimethyl heptyldimethylphosphonate (1.1 mmole, 1.5 eq.). The mixture was stirred for 1 hour at 25° C., cooled to 0° C. and a solution of 210 mg title D aldehyde (0.73 mmole) in 3 ml of dry DME added. The reaction mixture was stirred for 1 hour at 25° C., then quenched with glacial actic acid, and concentrated. The residue was diluted with 30 ml ether and washed with two 10 ml portions of saturated NaHCO$_3$, 10 ml of H$_2$O, dried over anhydrous MgSO$_4$ and concentrated to give an oil.

Purification was done on a silica gel column, eluting with 30% ether/hexane to give 200 ml of title enone as a yellow oil.

F.
[1α,2β,3β(1E,3R),4α]-5-[[[3-(3-Hydroxy-4,4-dimethyl-1-octenyl)-7-oxabicyclo[2.2.1]hept-2-yl]methyl]thio]pentanoic acid, methyl and ethyl esters To 200 mg of title E enone (0.49 mmole) in 2 ml of dry methanol at 25° C. was added 180 mg of cerium trichloride (0.49 mmole, 1 eq.). The mixture was stirred at 25° C. for 10 minutes, cooled to 0° C. then 18.6 mg of sodium borohydride (0.49 mmole, 4 eq.) was added. The reaction mixture was stirred at 0° C. for 15 minutes, then poured into 100 ml of saturated ammonium chloride solution and extracted with three 30 ml portions of ether. The combined ethereal extract was dried over anhydrous MgSO$_4$ and concentrated.

Purification and separation was done on a silica gel column, eluting with 33% ether in hexanes to give 133.5 mg of title allylic alcohol.

EXAMPLE 6
[1α,2β,3β(1E,3R),4α]-5-[[[3-(3-Hydroxy-4,4-dimethyl-1-octenyl)-7-oxabicyclo[2.2.1]hept-2-yl]methyl]thio]pentanoic acid To a solution of 133.5 mg of Example 5 ester (0.32 mmole) in 4 ml THF and 1 ml H$_2$O, saturated with argon, at 0° C. was added dropwise 3.2 ml of 1N lithium hydroxide solution. The mixture was stirred at 25° C. for 24 hours. THF was evaporated. The residue was diluted with 5 ml H$_2$O and acidified to pH 3 with a saturated oxalic acid solution and extracted with three 20 ml portions of ether. The ethereal extracts were washed with 10 ml H$_2$O, dried over anhydrous MgSO$_4$ and filtered through a pad of LPS-1 silica gel. The filtrate was concentrated to give 128.8 mg of title compound as a yellow oil.

TLC: Silica gel: 5% MeOH/CH$_2$Cl$_2$; R$_f$ 0.37.

Anal Calcd for C$_{22}$H$_{38}$O$_4$S: C, 66.39; H, 9.61; S, 8.04. Found: C, 65.89; H, 9.57; S, 7.82.

EXAMPLE 7
(1α,2β,3β,4α)-4-[[[3-(3-Hydroxy-4,4-dimethyloctyl)-7-oxabicyclo[2.2.1]hept-2-yl]ethyl]thio]butanoic acid, methyl ester A mixture of 410 mg of Example 1, title N allylic alcohol (1 mmole) and 500 mg of 10% palladium on charcoal in 10 ml of methanol is shaken in a Parr bottle under 40 psi hydrogen pressure. After 24 hours at 25° C., the catalyst is filtered and the methanol solution is concentrated to give the above title ester.

EXAMPLE 8
(1α,2β,3β,4α)-4-[[[3-(3-Hydroxy-4,4-dimethyloctyl)-7-oxabicyclo[2.2.1]hept-2-yl]ethyl]thio]butanoic acid Following the procedure of Example 2 except substituting the Example 7 ester for the Example 1 ester, the title acid is obtained.

EXAMPLE 9
[1α,2β,3β(1E,3R),4α]-4-[[[3-(3-Hydroxy-4,4-dimethyl-1-octenyl)-7-oxabicyclo[2.2.1]hept-2-yl]propyl]thio]-2-butenoic acid

A.
(1α,2β,3β,4α)-[3-t-Butyldimethylsilyloxy-7-oxabicyclo[2.2.1]hept-2-yl]propionaldehyde Into a dry 1000 ml round bottom 3-necked flask containing a stir bar is added dried 12.9 g (37.7 mmoles) methoxymethyltriphenylphosphonium chloride ((C$_6$H$_5$)$_3$P$^+$-CH$_2$OCH$_3$Cl$^-$) and 235 ml distilled toluene (stored over molecular sieves). The resulting suspension is stirred in an ice-bath, under argon, until cold and then a 1.55M solution of 18.3 ml (28.3 mmol) of potassium t-amylate in toluene is added dropwsie. A bright red solution forms which is stirred at 0° C. for an additional 35 minutes. Thereafter, a solution of 5.34 g (18.8 mmol) of Example 1 title F aldehyde in 60 ml toluene is added by means of a dropping funnel over a 35 minute period with the ice-bath still in place. The reaction is then quenched by addition of 2.3 g (39 mmol) acetic acid in 5 ml ether. The reaction mixture immediately turns pale yellow and is immediately poured into 200 ml saturated NH$_4$Cl, and extracted with ether (4×200 ml). The combined ether phases are washed with NaCl, saturated solution, and dried (MgSO$_4$) and concentrated to yield an oil in a white crystalline solid (phosphine oxide). The white solid is triturated with ether and filtered. The mother liquor is concentrated in vacuo, dissolved in tetrahydrofuran and stirred with 20% aqueous trifluoroacetic acid. After 2 hours at 25° C., solid sodium bicarbonate is added to quench the acid. The reaction mixture is diluted with ether, washed with water, dried over anhydrous magnesium sulfate and concentrated under reduced pressure. The crude residue is chromatographed on an LPS-1 silica gel column to obtain pure title A aldehyde.

B.
[1α,2β,3β(1E,3R),4α]-4-[[[3-(3-Hydroxy-4,4-dimethyl-1-octenyl)-7-oxabicyclo[2.2.1]hept-2-yl]propyl]thio]-2-butenoic acid Following the procedure of Examples 1 and 2 except substituting the above part A aldehyde for the aldehyde of Example 1, Part F, the title compound is obtained.

EXAMPLE 10

[1α,2β,3β(1E,3R),4α]-4-[[[3-(3-Hydroxy-4,4-dimethyl-1-octenyl)-7-oxabicyclo[2.2.1]hept-2-yl]butyl]thio]-2-butenoic acid A.
(1α,2β,3β,4α)-[3-t-Butyldimethylsilyloxy-7-oxabicyclo[2.2.1]hept-2-yl]butyraldehyde Following the procedure of Example 9, Part A except substituting the Example 9, title A compound for the Example 1, title F aldehyde, the title aldehyde is obtained.

B.
[1α,2β,3β(1E,3R),4α]-4-[[[3-(3-Hydroxy-4,4-dimethyl-1-octenyl)-7-oxabicyclo[2.2.1]hept-2-yl]butyl]thio]-2-butenoic acid Following the procedure of Examples 1 and 2 except substituting the title A aldehyde for the aldehyde of Example 1, Part F, the title compound is obtained.

EXAMPLE 11

[1α,2β,3β(1E,3R),4α]-5-[[[3-(3-Hydroxy-4,4-dimethyl-1-octenyl)-7-oxabicyclo[2.2.1]hept-2-yl]ethyl]thio]-3-pentenoic acid Following the procedure of Examples 1 and 2 except substituting methyl-5-bromo-3-pentenoate for methyl-4-bromocrotonate, the title compound is obtained.

EXAMPLE 12

[1α,2β,3β(1E,3R),4α]-6-[[3-(3-Hydroxy-4,4-dimethyl-1-octenyl)-7-oxabicyclo[2.2.1]-2-yl]ethyl]thio]-4-hexenoic acid Following the procedure of Examples 1 and 2 except substituting methyl-6-bromo-4-hexenoate for methyl-4-bromocrotonate, the title compound is obtained.

EXAMPLE 13

[1α,2β,3β(1E,3R),4α]-8-[[2-[3-(3-Hydroxy-4,4-dimethyl-1-octenyl)-7-oxabicyclo[2.2.1]hept-2-yl]ethyl]thio]-6-octenoic acid Following the procedure of Examples 1 and 2 except substituting methyl-8-bromo-6-octenoate for methyl-4-bromocrotonate, the title compound is obtained.

EXAMPLE 14

[1α,2β,3β(1E,3R),4α]-4-[[[3-(3-Hydroxy-3-cyclohexyl-1-propenyl)-7-oxabicyclo[2.2.1]hept-2-yl]ethyl]thio]-2-butenoic acid Following the procedure of Examples 1 and 2 except substituting 2-oxo-2-cyclohexyldimethylphosphonate for 2-oxo-3,3-dimethyl heptyldimethylphosphonate, the title compound is obtained.

EXAMPLE 15

[1α,2β,3β(1E,3R),4α]-4-[[[3-(3-Hydroxy-4-cyclohexyl-1-butenyl)-7-oxabicyclo[2.2.1]hept-2-yl]ethyl]thio]-2-butenoic acid Following the procedure of Examples 1 and 2 except substituting 2-oxo-2-cyclohexylmethyldimethylphosphonate for 2-oxo-3,3-dimethyl heptyldimethylphosphonate, the title compound is obtained.

EXAMPLE 16

[1α,2β,3β(1E,3R),4α]-4-[[[3-(3-Hydroxy-3-phenyl-1-propenyl)-7-oxabicyclo[2.2.1]hept-2-yl]ethyl]thio]-2-butenoic acid Following the procedure of Examples 1 and 2 except substituting 2-oxo-2-phenyl-dimethylphosphonate for 2-oxo-3,3-dimethyl heptyldimethylphosphonate, the title compound is obtained.

EXAMPLE 17

[1α,2β,3β(1E,3R),4α]-4-[[[3-(3-Hydroxy-3-benzyl-1-propenyl)-7-oxabicyclo[2.2.1]hept-2-yl]ethyl]thio]-2-butenoic acid Following the procedure of Examples 1 and 2 except substituting 2-oxo-2-benzyl-dimethylphosphonate for 2-oxo-3,3-dimethyl heptyldimethylphosphonate, the title compound is obtained.

EXAMPLE 18

[1α,2β,3β(1E,3R),4α]-4-[[[3-(3-Hydroxy-3-hexyl-1-propenyl)-7-oxabicyclo[2.2.1]hept-2-yl]ethyl]thio]-2-butenoic acid Following the procedure of Examples 1 and 2 except substituting 2-oxo-2-hexyl-dimethylphosphonate for 2-oxo-3,3-dimethyl heptyldimethylphosphonate, the title compound is obtained.

EXAMPLE 19

[1α,2β,3β(1E,3R),4α]-4-[[[3-(3-Hydroxy-3-pentyl-1-propenyl)-7-oxabicyclo[2.2.1]hept-2-yl]ethyl]thio]pentanoic acid Following the procedure of Examples 1, part K, 3 and 4 except substituting methyl-5-bromo-3-pentenoate for methyl-4-bromocrotonate and substituting 2-oxo-2-pentyldimethylphosphonate for 2-oxo-3,3-dimethyl heptyl dimethylphosphonate, the title compound is obtained.

EXAMPLE 20

[1α,2β,3β(1E,3R),4α]-6-[[[3-(3-Hydroxy-3-phenyl-1-propenyl)-7-oxabicyclo[2.2.1]hept-2-yl]ethyl]thio]-5-hexenoic acid Following the procedure of Examples 1 and 2 except substituting methyl-6-bromo-5-hexenoate for methyl-4-bromocrotonate and substituting 2-oxo-2-phenyl-dimethylphosphonate for 2-oxo-3,3-dimethyl heptyl dimethylphosphonate, the title compound is obtained.

EXAMPLE 21

[1α,2β,3β(1E,3R),4α]-5-[[[3-(3-Hydroxy-3-cyclopentyl-1-propenyl)-7-oxabicyclo[2.2.1]hept-2-yl]ethyl]thio]-4-pentenoic acid Following the procedure of Examples 1 and 2 except substituting methyl-5-bromo-4-pentenoate for methyl-4-bromocrotonate and substituting 2-oxo-2-cyclopentyldimethylphosphonate for 2-oxo-3,3-dimethyl heptyl dimethylphosphonate, the title compound is obtained.

EXAMPLE 22

[1α,2β,3β(1E,3R),4α]-4-[[[3-(3-Hydroxy-4-cyclohexyl-1-butenyl)-7-oxabicyclo[2.2.1]hept-2-yl]ethyl]thio]butanoic acid Following the procedure of Examples 3 and 4 except substituting 2-oxo-2-cyclohexylmethyldimethylphosphonate for 2-oxo-3,3-dimethylheptyldimethylphosphonate, the title compound is obtained.

EXAMPLE 23

[1α,2β,3β(1E,3R),4α]-4-[[[3-(3-Hydroxy-3-cyclohexyl)-7-oxabicyclo[2.2.1]hept-2-yl]ethyl]thio]butanoic acid Following the procedure of Examples 3 and 4 except substituting 2-oxo-2-cyclohexyldimethylphosphonate for 2-oxo-3,3-dimethylheptyldimethylphosphonate, the title compound is obtained.

EXAMPLE 24

[1α,2β,3β(1E,3R),4α]-4-[[[3-(3-Hydroxy-3-phenyl-1-propenyl)-7-oxabicyclo[2.2.1]hept-2-yl]ethyl]thio]butanoic acid Following the procedure of Examples 3 and 4 except substituting 2-oxo-2-propenyldimethylphosphonate for 2-oxo-3,3-dimethylheptyldimethylphosphonate, the title compound is obtained.

EXAMPLE 25

[1α,2β,3β(1E,3R),4α]-4-[[[3-(3-Hydroxy-3-phenethyl-1-propenyl)-7-oxabicyclo[2.2.1]hept-2-yl]ethyl]thio]butanoic acid Following the procedure of Examples 3 and 4 except substituting 2-oxo-2-phenethyldimethylphosphonate for 2-oxo-3,3-dimethylheptyldimethylphosphonate, the title compound is obtained.

EXAMPLE 26

[1α,2β,3β(1E,3R),4α]-4-[[[3-(3-Hydroxy-3-butyl-1-propenyl)-7-oxabicyclo[2.2.1]hept-2-yl]ethyl]thio]butanoic acid Following the procedure of Examples 3 and 4 except substituting 2-oxo-2-butyl-dimethylphosphonate for 2-oxo-3,3-dimethyl heptyldimethylphosphonate, the title compound is obtained.

EXAMPLE 27

[1α,2β,3β(1E,3R),4α]-4-[[[3-(3-Hydroxy-4,4-dimethyl-1-octenyl)-7-oxabicyclo[2.2.1]hept-2-yl]methyl]thio]butanoic acid Following the procedure of Examples 5 and 6 except substituting ethyl-4-bromobutanoate for ethyl-5-bromovalerate, the title compound is obtained.

EXAMPLE 28

[1α,2β,3β(1E,3R),4α]-6-[[[3-(3-Hydroxy-4,4-dimethyl-1-octenyl)-7-oxabicyclo[2.2.1]hept-2-yl]methyl]thio]hexanoic acid Following the procedure of Examples 5 and 6 except substituting methyl-6-bromohexanoate for ethyl-5-bromovalerate, the title compound is obtained.

EXAMPLE 29

[1α,2β,3β(1E,3R),4α]-7-[[[3-(3-Hydroxy-4,4-dimethyl-1-octenyl)-7-oxabicyclo[2.2.1]hept-2-yl]methyl]thio]heptanoic acid Following the procedure of Examples 5 and 6 except substituting ethyl-7-bromoheptanoate for ethyl-5-bromovalerate, the title compound is obtained.

EXAMPLE 30

[1α,2β,3β(1E,3R),4α]-8-[[[3-(3-Hydroxy-4,4-dimethyl-1-octenyl)-7-oxabicyclo[2.2.1]hept-2-yl]methyl]thio]octanoic acid Following the procedure of Examples 5 and 6 except substituting methyl-8-bromooctanoate for ethyl-5-bromovalerate, the title compound is obtained.

EXAMPLE 31

[1α,2β,3β(1E,3R),4α]-3-[[[3-(3-Hydroxy-4,4-dimethyl-1-octenyl)-7-oxabicyclo[2.2.1]hept-2-yl]methyl]thio]propionic acid Following the procedure of Examples 5 and 6 except substituting methyl-3-bromopropionate for ethyl-5-bromovalerate, the title compound is obtained.

EXAMPLE 32

[1α,2β,3β(1E,3R),4α]-5-[[[3-(3-Hydroxy-3-cyclohexyl)-7-oxabicyclo[2.2.1]hept-2-yl]methyl]thio]pentanoic acid Following the procedure of Examples 5 and 6 except substituting 2-oxo-2-cyclohexyldimethylphosphonate for 2-oxo-3,3-dimethylheptyldimethylphosphonate, the title compound is obtained.

EXAMPLE 33

[1α,2β,3β(1E,3R),4α]-5-[[[3-(3-Hydroxy-5-cyclohexyl-1-pentenyl)-7-oxabicyclo[2.2.1]hept-2-yl]methyl]thio]pentanoic acid Following the procedure of Examples 5 and 6 except substituting 2-oxo-2-cyclohexylethyldimethylphosphonate for 2-oxo-3,3-dimethylheptyldimethylphosphonate, the title compound is obtained.

EXAMPLE 34

[1α,2β,3β(1E,3R),4α]-5-[[[3-(3-Hydroxy-3-phenyl)-7-oxabicyclo[2.2.1]hept-2-yl]methyl]thio]pentanoic acid Following the procedure of Examples 5 and 6 except substituting 2-oxo-2-phenyl-dimethylphosphonate for 2-oxo-3,3-dimethylheptyldimethylphosphonate, the title compound is obtained.

EXAMPLE 35

[1α,2β,3β(1E,3R),4α]-5-[[[3-(3-Hydroxy-3-benzyl-1-propenyl)-7-oxabicyclo[2.2.1]hept-2-yl]methyl]thio]-pentanoic acid Following the procedure of Examples 5 and 6 except substituting 2-oxo-2-benzyl-dimethylphosphonate for 2-oxo-3,3-dimethyl heptyldimethylphosphonate, the title compound is obtained.

EXAMPLE 36

[1α,2β,3β(1E,3R),4α]-5-[[[3-(3-Hydroxy-3-pentyl-1-propenyl)-7-oxabicyclo[2.2.1]hept-2-yl]methyl]thio]-pentanoic acid Following the procedure of Examples 5 and 6 except substituting 2-oxo-2-pentyl-dimethylphosphonate for 2-oxo-3,3-dimethyl heptyldimethylphosphonate, the title compound is obtained.

EXAMPLE 37

[1α,2β,3β(1E,3R),4α]-6-[[[3-(3-Hydroxy-3-benzyl-1-propenyl)-7-oxabicyclo[2.2.1]hept-2-yl]methyl]thio]-hexanoic acid Following the procedure of Examples 5 and 6 except substituting ethyl-6-bromohexanoate for ethyl-5-bromovalerate and substituting 2-oxo-2-benzyl dimethylphosphonate for 2-oxo-3,3-dimethyl heptyl dimethylphosphonate, the title compound is obtained.

EXAMPLE 38

[1α,2β,3β(1E,3R),4α]-7-[[[3-(3-Hydroxy-3-phenyl-1-propenyl)-7-oxabicyclo[2.2.1]hept-2-yl]methyl]thio]-7-heptanoic acid Following the procedure of Examples 5 and 6 except substituting methyl-7-bromoheptanoate for ethyl-5-bromovalerate and substituting 2-oxo-2-phenyl dimethylphosphonate for 2-oxo-3,3-dimethyl heptyl dimethylphosphonate, the title compound is obtained.

EXAMPLE 39

[1α,2β,3β(1E,3R),4α]-6-[[[3-(3-Hydroxy-3-cyclopentyl-1-propenyl)-7-oxabicyclo[2.2.1]hept-2-yl]methyl]-thio]-2-hexenoic acid Following the procedure of Examples 5 and 6 except substituting ethyl-6-bromo-2-hexenoate for ethyl-5-bromovalerate and substituting 2-oxo-2-cyclopentyl dimethylphosphonate for 2-oxo-3,3-dimethyl heptyl dimethylphosphonate, the title compound is obtained.

EXAMPLE 40

[1α,2β,3β(1E,3R),4α]-5-[[[3-(3-Hydroxy-4-cyclohexyl-1-butenyl)-7-oxabicyclo[2.2.1]hept-2-yl]methyl]thio]-2-pentenoic acid Following the procedure of Examples 5 and 6 except substituting methyl-5-bromo-2-pentenoate for ethyl-5-bromovalerate and substituting 2-oxo-2-cyclohexyl-methyl dimethylphosphonate for 2-oxo-3,3-dimethyl heptyl dimethylphosphonate, the title compound is obtained.

EXAMPLE 41

(1α,2β,3β,4α)-4-[[[3-(3-Hydroxy-4,4-dimethyloctyl)-7-oxabicyclo[2.2.1]hept-2-yl]methyl]thio]butanoic acid Following the procedure of Examples 5, 7 and 8 except substituting methyl-4-bromobutyrate for ethyl-5-bromovalerate, the title compound is obtained.

EXAMPLE 42

(1α,2β,3β,4α)-4-[[[3-(3-Hydroxy-3-phenylpropyl)-7-oxabicyclo[2.2.1]hept-2-yl]ethyl]thio]-2-butenoic acid Following the procedure of Examples 1, 7 and 8 except substituting 2-oxo-2-phenethyl dimethylphosphonate for 2-oxo-3,3-dimethylheptyl dimethylphosphonate, the title compound is obtained.

EXAMPLE 43

(1α,2β,3β,4α)-4-[[[3-(3-Hydroxy-3-cyclohexylpropyl)-7-oxabicyclo[2.2.1]hept-2-yl]ethyl]thio]-2-butenoic acid Following the procedure of Examples 1, 7 and 8 except substituting 2-oxo-2-cyclohexylethyldimethyl phosphonate for 2-oxo-3,3-dimethylheptyldimethyl phosphonate, the title compound is obtained.

EXAMPLE 44

(1α,2β,3β,4α)-5-[[[3-(3-Hydroxy-4,4-dimethyloctyl)-7-oxabicyclo[2.2.1]hept-2-yl]methyl]thio]pentanoic acid Following the procedure of Examples 1, 3 Part A, 7 and 8 except substituting ethyl-5-bromopentenoate for methyl-4-bromocrotonate, the title compound is obtained.

EXAMPLE 45

(1α,2β,3β,4α)-3-[[[3-(3-Hydroxy-4,4-dimethyloctyl)-7-oxabicyclo[2.2.1]hept-2-yl]methyl]phenoxy]propionic acid Following the procedure of Examples 1, 3 Part A, 7 and 8 except substituting methyl-3-bromopropenoate for methyl-4-bromocrotonate, the title compound is obtained.

EXAMPLE 46

[1α,2β,3β(1E,3R),4α]-4-[[[3-(3-Hydroxy-4,4-dimethyl-1-octenyl)-7-oxabicyclo[2.2.1]hept-2-yl]propyl]thio]-butanoic acid Following the procedure of Examples 7 and 8, except substituting Example 9, Part B allylic alcohol, methyl ester for Example 1, Part N allylic alcohol, methyl ester, the title acid is obtained.

EXAMPLE 47

[1α,2β,3β(1E,3R),4α]-5-[[[3-(3-Hydroxy-4,4-dimethyl-1-octenyl)-7-oxabicyclo[2.2.1]hept-2-yl]propyl]thio]-pentanoic acid Following the procedure of Examples 9, 1, 7 and 8 except substituting ethyl-5-bromopentenoate for methyl-4-bromocrotonate, the title acid is obtained.

EXAMPLE 48

[1α,2β,3β(1E,3R),4α]-4-[[[3-(3-Hydroxy-3-cyclohexyl-1-propenyl)-7-oxabicyclo[2.2.1]hept-2-yl]propyl]thio]-2-butenoic acid Following the procedure of Examples 9, 1 and 2 except substituting 2-oxo-2-cyclohexyl dimethyl-phos-

EXAMPLE 49

[1α,2β,3β(1E,3R),4α]-4-[[[3-(3-Hydroxy-3-phenyl-1-propenyl)-7-oxabicyclo[2.2.1]hept-2-yl]propyl]thio]butanoic acid Following the procedure of Examples 9, 1, 3 and 4 except substituting 2-oxo-2-phenylhexylethyl dimethylphosphonate for 2-oxo-3,3-dimethylheptyl dimethylphosphonate, the title acid is obtained.

EXAMPLE 50

(1α,2β,3β,4α)-5-[[[3-(3-Hydroxy-4,4-dimethyloctyl)-7-oxabicyclo[2.2.1]hept-2-yl]propyl]thio]pentanoic acid Following the procedure of Examples 7, 1, 3 and 4, except substituting ethyl-5-bromo-3-pentenoate for methyl-4-bromocrotonate, the title acid is obtained.

EXAMPLE 51

[1α,2β,3β(1E,3R),4α]-4-[[[3-(3-Hydroxy-4,4-dimethyl-1-octenyl)-7-oxabicyclo[2.2.1]hept-2-yl]butyl]thio]butanoic acid Following the procedure of Examples 1, 3 and 4, except substituting Example 9, title A aldehyde for Example 1, title F aldehyde, the title acid is obtained.

EXAMPLE 52

[1α,2β,3β(1E,3R),4α]-4-[[[3-(3-Hydroxy-3-phenylpropyl)-7-oxabicyclo[2.2.1]hept-2-yl]butyl]thio]-2-butenoic acid Following the procedure of Examples 10, 1 and 2, except substituting 2-oxo-phenethyl dimethylphosphonate for 2-oxo-3,3-dimethylheptyldimethylphosphonate, the title acid is obtained.

EXAMPLE 53

[1α,2β,3β(1E,3R),4α]-5-[[[3-(3-Hydroxy-3-cyclohexylpropyl)-7-oxabicyclo[2.2.1]hept-2-yl]butyl]thio]pentanoic acid Following the procedure of Examples 10, 1, 3 and 4, except substituting ethyl-5-bromopentenoate for methyl-4-bromocrotonate and substituting 2-oxo-2-cyclohexylethyl dimethylphosphonate for 2-oxo-3,3-dimethylheptyl dimethylphosphonate, the title acid is obtained.

What is claimed is:

1. A compound of the structure

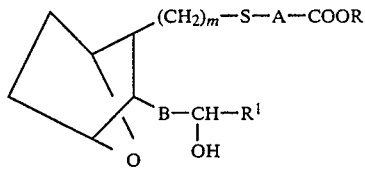

including all stereoisomers thereof, wherein m is 1 to 4, A is $(CH_2)_n$ or $-(CH_2)_{n'}$ $-CH=CH-$; n is 1 to 8; n' is 1 or 2; B is $-CH=CH-$ or $-(CH_2)_2-$; R is H, lower alkyl or alkali metal; and $R^1$ is lower alkyl, aryl, arylalkyl, cycloalkyl or cycloalkylalkyl; wherein the term lower alkyl or alkyl by itself or as part of another group is unsubstituted or substituted with halo, trifluoromethyl, alkoxy, aryl, alkyl-aryl, haloaryl, cycloalkyl, or alkylcycloalkyl; the term aryl by itself or as part of another group contains 6 to 10 carbons and is unsubstituted or substituted with lower alkyl, halogen or lower alkoxy; and the term cycloalkyl by itself or as part of another group contains 3 to 12 carbons and is unsubstituted or is substituted with 1 or 2 halogens, 1 or 2 lower alkyl groups and/or 1 or 2 lower alkoxy groups; and wherein $(CH_2)_m$ or $(CH_2)_n$ may be substituted by one or more lower alkyl substituents.

2. The compound as defined in claim 1 wherein B is $-CH=CH-$.

3. The compound as defined in claim 1 wherein R is H.

4. The compound as defined in claim 1 wherein A is $(CH_2)_n$ and n is 2 to 5.

5. The compound as defined in claim 1 wherein n is 3 or 4.

6. The compound as defined in claim 1 wherein B is $-CH=CH-$, m is 1 or 2, A is $(CH_2)_n$, n is 3 or 4, R is H and $R^1$ is lower alkyl.

7. The compound as defined in claim 1 wherein $R^1$ is butyl, pentyl, hexyl or heptyl including all isomers thereof.

8. The compound as defined in claim 1 having the name [1α,2β,3β(1E,3R),4α]-4-[[[3-(3-hydroxy-4,4-dimethyl-1-octenyl)-7-oxabicyclo[2.2.1]hept-2-yl]ethyl]thio]-2-butenoic acid or the methyl ester thereof, including all stereoisomers thereof.

9. The compound as defined in claim 1 having the name [1α,2β,3β(1E,3R),4α]-5-[[[3-(3-hydroxy-4,4-dimethyl-1-octenyl)-7-oxabicyclo[2.2.1]hept-2-yl]methyl]thio]pentanoic acid or the methyl ester thereof, including all stereoisomers thereof.

10. The compound as defined in claim 1 having the same [1α,2β,3β(1E,3R),4α]-4-[[[3-(3-hydroxy-4,4-dimethyl-1-octenyl)-7-oxabicyclo[2.2.1]hept-2-yl]ethyl]thio]butanoic acid or the methyl ester thereof, including all stereoisomers thereof.

11. A method of inhibiting arachidonic acid-induced platelet aggregation and bronchoconstriction, which comprises administering to the circuitry system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,524,151
DATED : June 18, 1985
INVENTOR(S) : Jagabandhu Das et al.

It is certified that error appears in the above—identified patent and that said Letters Patent is hereby corrected as shown below:

Column 7, structure IVA should read

-- 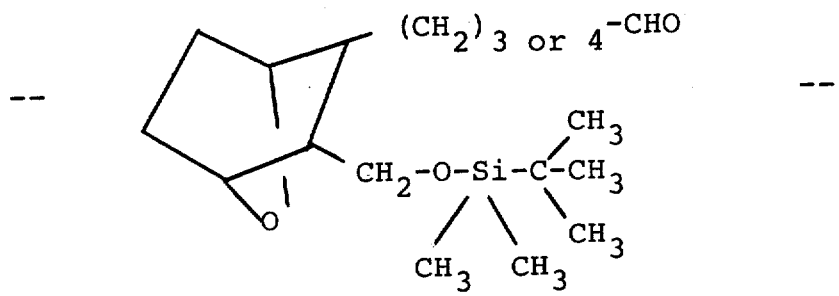 --

Column 11, structures Ia, Ib, Ic and Id should read as follows.

-- Ia 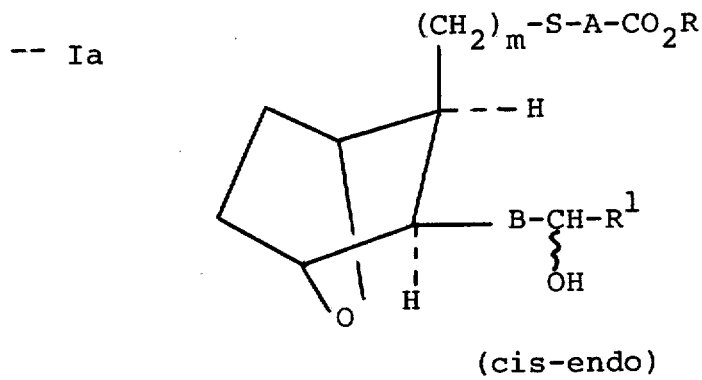

(cis-endo)

UNITED STATES PATENT AND TRADEMARK OFFICE
CERTIFICATE OF CORRECTION

PATENT NO. : 4,524,151
DATED : June 18, 1985
INVENTOR(S) : Jagabandhu Das et al.

It is certified that error appears in the above—identified patent and that said Letters Patent is hereby corrected as shown below:

Ib

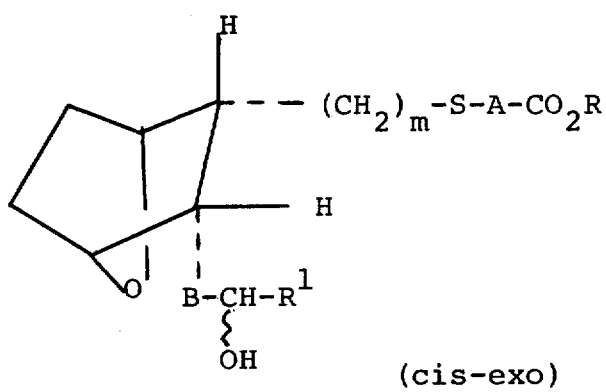

(cis-exo)

Ic

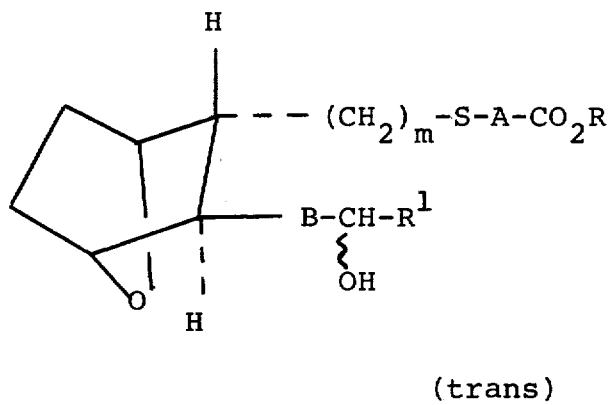

(trans)

UNITED STATES PATENT AND TRADEMARK OFFICE
CERTIFICATE OF CORRECTION

PATENT NO. : 4,524,151
DATED : June 18, 1985
INVENTOR(S) : Jagabandhu Das et al.

It is certified that error appears in the above—identified patent and that said Letters Patent is hereby corrected as shown below:

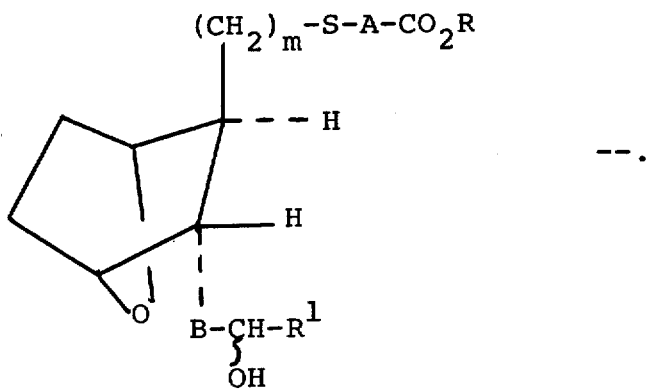

Column 11, line 54, "wavy ( )" should read --wavy ($)--.
Column 18, line 26, "1.43 g" should read --1.43 ml--.
Column 27, line 61, "-(CH$_2$)$_n$,-CH=CH-" should read
-- -(CH$_2$)$_{n'}$-CH=CH- --.
Column 28, line 41, "circuitry" should read --circulatory--.

Signed and Sealed this

Eighth Day of October 1985

[SEAL]

Attest:

DONALD J. QUIGG

Attesting Officer

Commissioner of Patents and
Trademarks—Designate